United States Patent [19]

Fischer

[11] Patent Number: 5,286,257
[45] Date of Patent: Feb. 15, 1994

[54] SYRINGE APPARATUS WITH DETACHABLE MIXING AND DELIVERY TIP

[75] Inventor: Dan E. Fischer, Sandy, Utah

[73] Assignee: Ultradent Products, Inc., South Jordan, Utah

[21] Appl. No.: 977,685

[22] Filed: Nov. 18, 1992

[51] Int. Cl.⁵ .......................................... A61M 37/00
[52] U.S. Cl. ..................................... 604/82; 604/87; 604/91; 604/311; 604/218; 604/416; 433/90; 222/136
[58] Field of Search .................... 604/82, 85–91, 604/191, 201, 203, 205, 244, 249, 416, 218, 187, 316, 311; 222/129, 136; 215/DIG. 8; 206/219, 221; 433/80, 89, 90

[56] References Cited
U.S. PATENT DOCUMENTS

| | | | |
|---|---|---|---|
| 3,028,052 | 4/1962 | Archer | 222/136 |
| 3,347,410 | 10/1967 | Schwartzman | 222/129 X |
| 3,370,754 | 2/1968 | Cook et al. | 222/136 X |
| 3,595,439 | 7/1971 | Newby | 222/136 X |
| 3,739,947 | 6/1973 | Baumann et al. | 222/136 |
| 3,767,085 | 10/1973 | Cannon et al. | 222/82 |
| 3,838,689 | 10/1974 | Cohen | 604/90 |
| 3,946,732 | 3/1976 | Hurscham | |
| 3,985,122 | 10/1976 | Topham | |
| 4,041,945 | 8/1977 | Guiney | 604/91 |
| 4,055,177 | 10/1977 | Cohen | |
| 4,059,109 | 11/1977 | Tischlinger | |
| 4,171,698 | 10/1979 | Genese | 604/88 |
| 4,203,517 | 5/1980 | Hildebrandt et al. | 206/221 |
| 4,234,083 | 11/1980 | Cohen | 206/221 |
| 4,340,056 | 7/1982 | Erb | 604/416 X |
| 4,424,057 | 1/1984 | House | 604/88 |
| 4,449,645 | 5/1984 | Korwin | 222/49 |
| 4,464,174 | 8/1984 | Ennis | 604/90 |
| 4,581,016 | 4/1986 | Gettig | 604/88 |
| 4,648,532 | 3/1987 | Green | 222/82 |
| 4,713,062 | 12/1987 | Stevanato | 604/203 |
| 4,808,184 | 2/1989 | Tepic | 604/56 |
| 4,993,948 | 2/1991 | Cameron et al. | 433/90 |
| 4,997,371 | 3/1991 | Fischer | 433/90 |
| 5,026,283 | 6/1991 | Osanai et al. | 433/90 |
| 5,172,807 | 12/1992 | Dragan et al. | 206/219 |

*Primary Examiner*—C. Fred Rosenbaum
*Assistant Examiner*—Mark O. Polutta
*Attorney, Agent, or Firm*—Workman Nydegger Jensen

[57] ABSTRACT

A syringe device having a barrel enclosing a first chamber therein containing coaxially aligned primary and secondary plungers. A connectable mixing and delivery tip encloses a second chamber therein and is connected to the barrel by a coupling. A slidable valve having an aperture therethrough to allow passage of air into and out of the secondchamber is disposed between the two chambers. The primary plunger is slidable out one end of the syringe for the selective application of pressure into the syringe barrel. As the primary plunger is urged down into the syringe barrel, air is forced around the secondary plunger and through the valve aperture into the second chamber wherein the substances contained therein are mixed by turbulent aeration. Continued application of pressure on the primary plunger drives the secondary plunger into the slidable valve to plug the aperture in the valve thereby ceasing the agitation of the contents in the second chamber. Further urging of the primary plunger drives the secondary plunger and the slidable valve up into the second chamber so that the mixed contents are expelled out of the syringe device through a delivery tip. With such a syringe mixing apparatus, substances can be mixed and expelled from the syringe by continued movement of the primary plunger into the syringe barrel.

16 Claims, 7 Drawing Sheets

SYRINGE APPARATUS WITH DETACHABLE MIXING AND DELIVERY TIP

BACKGROUND

1. Field of the Invention

Broadly conceived, the present invention relates to syringes. More particularly, the present invention relates to a syringe mixing apparatus wherein a plurality of substances can be first mixed together and then expelled all from a single delivery tip.

2. The Prior Art

In the field of dentistry, there are many types of procedures that require the mixing of two or more substances before the mixed compound can be used in a particular dental procedure. A common practice in the dental arts is to measure the separate substances dropwise into a well or mixing dish and to then mix the separate substances together using an applicator brush, which in turn is then used to apply the mixed compound to the desired teeth surfaces. As will be appreciated, in dentistry it is often necessary to mix relatively small amounts because of the small surface areas that are to be worked upon. Furthermore, the materials which are mixed are often expensive and therefore, rather than mix larger quantities, relatively small quantities are mixed repeatedly so as not to waste undue amounts of the materials in question. Repeated mixing, of course, becomes tedious and time consuming.

The described procedure also suffers from other disadvantages. For example, when mixing separate substances in a well or mixing dish with an applicator brush, the applicator brush must be moved from the mixing well into the patient's mouth for purposes of applying the mixed substance to the tooth surfaces, then back to the mixing well to obtain fresh quantities of the mixed substance and then back to the patient's mouth again. This type of back and forth motion between the patient's mouth and mixing well means that each time the brush is removed from the patient's mouth, the applicator brush must be repositioned with the tooth surface when it is inserted back into the patient's mouth. Furthermore, there is added risk of inadvertently touching the lips, gums, or other parts of the mouth by virtue of having to reposition the applicator brush with the tooth surface each time the brush is removed back to the mixing well to obtain fresh quantities of the mixed substance on the brush applicator. Not only does this create the possibility of irritating the patient's lips, gums, or other tissue, but it also creates the possibility of contaminating the mixed substance with saliva, so as to change the composition of the mixed substance in an undesirable way.

Further problems with the described procedure arise in connection with the potential bacterial contamination to the mixing well or dish by repeated moving of the applicator brush from the patient's mouth to the mixing well. This creates the need to sterilize the mixing well, which adds additional expense and time to office procedures, as well as creating potential risk for contamination of other patients if the mixing well is not properly sterilized between patients. Alternatively, if the mixing well is made of materials so as to be disposable, this adds an increased burden on the environment since typically such materials are made of plastics.

Still other problems in connection with the described procedure may arise where the substances that are mixed are of a relatively low viscosity. In order to obtain a sufficient quantity of the material when using an applicator brush, the brush tip typically has to be made somewhat larger so that the required quantities of materials can be carried to the mouth. However, the larger size applicator brush makes precise placement and working of the materials more difficult and thus results in a less precise delivery of the materials to the desired tooth surfaces.

Yet a further problem is that even once the substances are mixed in the mixing well, for some types of substances evaporation can become a problem. For example, it is common to mix hydrophilic resins in acetone for use in certain types of bonding procedures used in dentistry. The acetone can evaporate rapidly if it is left sitting very long in a mixing well, and this can adversely change the concentration of the mixed substance so as to change the bonding characteristics of the mixed substance. This further complicates the procedure and may require repeated mixing rather than using larger quantities of the mixed substance. As will be appreciated, this, of course, also adds to the tedium, expense and the difficulty of the overall procedure.

OBJECTS AND SUMMARY OF THE INVENTION

The apparatus of the present invention seeks to resolve the above and other problems which have been experienced in the art. More particularly, the present invention provides an improved syringe mixing apparatus as is evidenced by the following objects and advantages realized by this invention over the prior art.

It is a primary object of the present invention to provide a syringe mixing apparatus which facilitates the mixing of two or more substances within a separate syringe tip which is used not only for the mixing of the substances, but which is also subsequently used for delivery of the mixed substances by actuation of the syringe plunger. This advantageously eliminates evaporation problems and also eliminates the need for repeatedly moving an applicator brush from the mouth of a patient back to a mixing well and thus permits the dental professional to keep the applicator brush positioned and in the mouth of the patient at the tooth surface which is being worked upon. This further eliminates the risk of contamination of the mixed substances as well as accidental contact with unwanted tissues such as the lips or gums of the patient by virtue of having to move the applicator brush into and out of the patient's mouth in repeated motions.

It is a further object of the present invention to provide a syringe mixing apparatus which facilitates mixing of two or more substances and then subsequent delivery of the mixed substances by means of continued movement of the syringe plunger into the syringe barrel.

Yet a further object of the present invention is to provide a syringe mixing and delivery apparatus which permits more exact delivery of the mixed substances in very small quantities and which provides for more precise control in the application of those mixed substances to small working surfaces.

Another important object of the present invention is to provide a syringe mixing and delivery apparatus which tends to minimize the amount of plastic material disposed by requiring disposal of only the syringe mixing and delivery tip, while permitting reuse of the standard syringe that is used with the mixing and delivery tip.

Still a further object of the present invention is to provide a syringe mixing apparatus which will find useful application not only in the dental or medical arts, but also in other industrial applications where the above or similar advantages may be put to practical use in such other arts.

These and other objects and features of the present invention will become more fully apparent from the following description and appended claims taken in conjunction with the accompanying drawings. Additional objects and advantages of the invention may be learned by the practice of the invention.

Briefly described, in one presently preferred embodiment of the apparatus of the present invention, the syringe apparatus is comprised of a standard syringe barrel with a plunger therein. The syringe barrel is couplable, for example, by means of a standard luer coupling, to a disposable delivery tip which also serves as a mixing chamber in which separate substances are to be mixed. Preferably the syringe barrel and delivery tip are constructed of materials that are transparent or semi-transparent to permit visual inspection of the contents and actuation of the plunger mechanism.

A small secondary piston which is preferably elastomeric is disposed in the end of the delivery tip after the substances have been placed therein, and the secondary piston has a small aperture through it for providing passage of air into and out of the mixing chamber. A primary plunger is situated in the syringe barrel in conventional fashion and has a primary piston which is also preferably an elastomeric material in fluid-tight engagement with the interior wall of the syringe barrel.

A secondary plunger is also situated within the syringe barrel and is moveable in tandem with the primary syringe plunger. In one presently preferred method for operating the apparatus of the present invention, as the primary syringe plunger is moved through the syringe barrel for a first distance, air is pressurized and is injected through the aperture in the secondary piston into the mixing chamber of the delivery tip to create bubbles, and hence a mixing turbulence which mixes the substances contained in the delivery tip. After the primary plunger has been moved through the first distance, continued movement of the primary plunger then causes contact with the secondary syringe plunger. This in turn seals the aperture of the secondary piston, so that continued movement of the primary plunger through a second distance by pushing it farther into the syringe barrel causes ejection of the now mixed substances through the delivery tip by virtue of the tandem movement of the secondary plunger and the secondary piston which has now been contacted and sealed at the end of the secondary plunger. Thus, as will be appreciated, by a single movement of the primary plunger, the substances placed in the mixing chamber of the delivery tip are first mixed by injection of air into the delivery tip to create a mixing turbulence, and then continued movement of the syringe plunger can be used to effect delivery of the mixed materials through the delivery tip.

In another preferred method for using the apparatus of the invention, prior to sealing the end of the mixing chamber of the delivery tip with the secondary piston, the substances which are placed into the mixing chamber can be mechanically mixed, for example, by using a small stir rod. The secondary plunger can thereafter seal the mixed substances in the delivery tip. According to this method for using the apparatus, there is then no need to inject air for purposes of mixing, and the primary plunger is used to simply contact the secondary plunger so as to effect sealing of the secondary piston and subsequent delivery of the mixed substances through the delivery tip by continued movement of the primary syringe plunger.

BRIEF DESCRIPTION OF THE DRAWINGS

In order to more fully understand the manner in which the above-recited and other advantages and objects of the invention are obtained, a more particular description of the invention will be rendered by reference to a specific embodiment and the presently understood best mode thereof which is illustrated in the appended drawings. Understanding that these drawings depict only a presently preferred embodiment of the invention and are not therefore to be considered limiting of its scope, the invention will be described and explained with additional specificity and detail through the use of the accompanying drawings in which.

DETAILED DESCRIPTION OF PREFERRED EMBODIMENTS

Reference is now made to the drawings wherein like parts are designated with like numerals throughout. In the following description, the inventive aspects of the syringe apparatus are illustrated in the drawings and in the accompanying description which follows in the context of a device which has been developed and designed particularly for application in the field of dentistry. However, as noted above briefly in the objects and summary of the invention, the broad inventive principles of this invention will also be able to be usefully employed by others skilled in the art in the context of any of a variety of different industrial or other applications. Thus, while the following detailed description describes the invention as particularly applied to the field of dentistry, that is not to be construed as limiting with respect to the broad scope of the invention as claimed.

Figure 1:
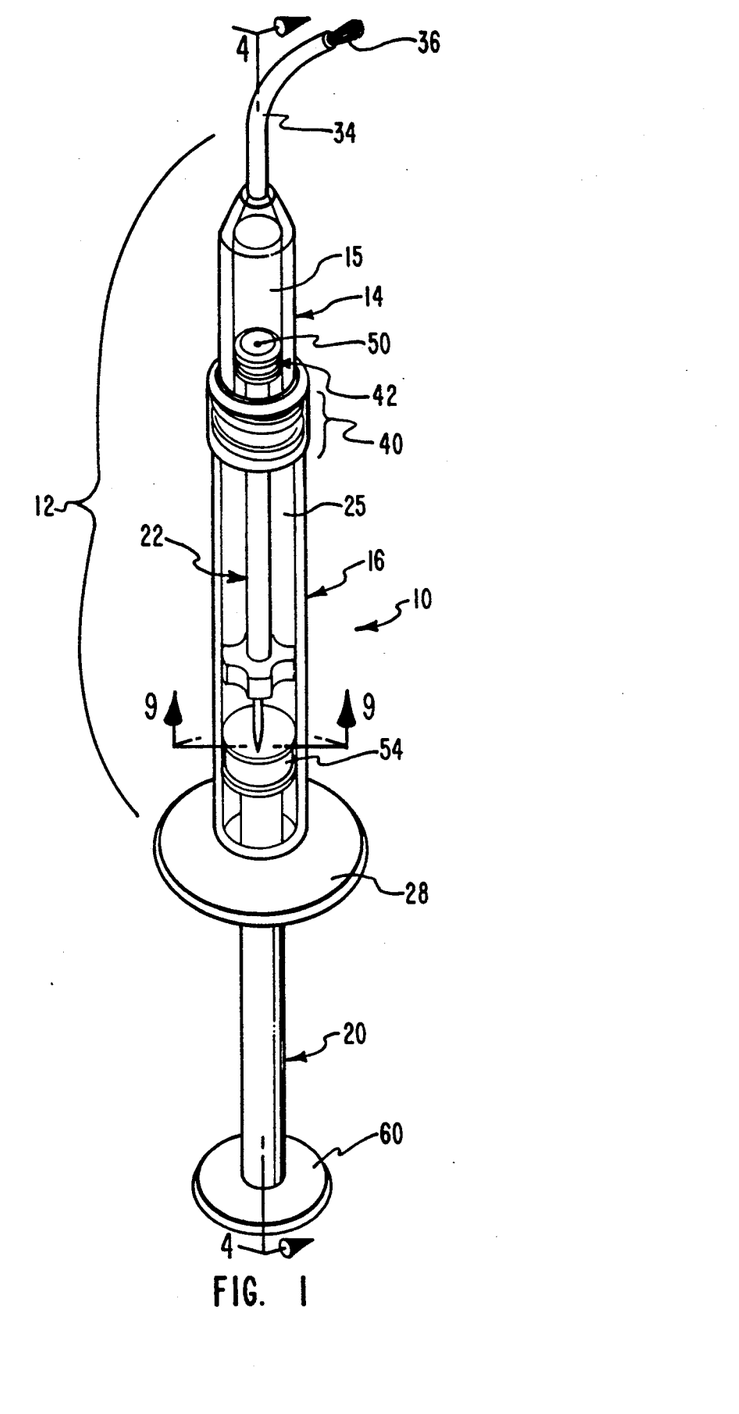
FIG. 1 is a perspective view of one embodiment of the syringe apparatus of the present invention illustrating the primary and secondary plungers contained within the syringe barrel and the attachment of the mixing and delivery tip enclosing a resilient slidable valve or secondary piston therein.
Figure 2:
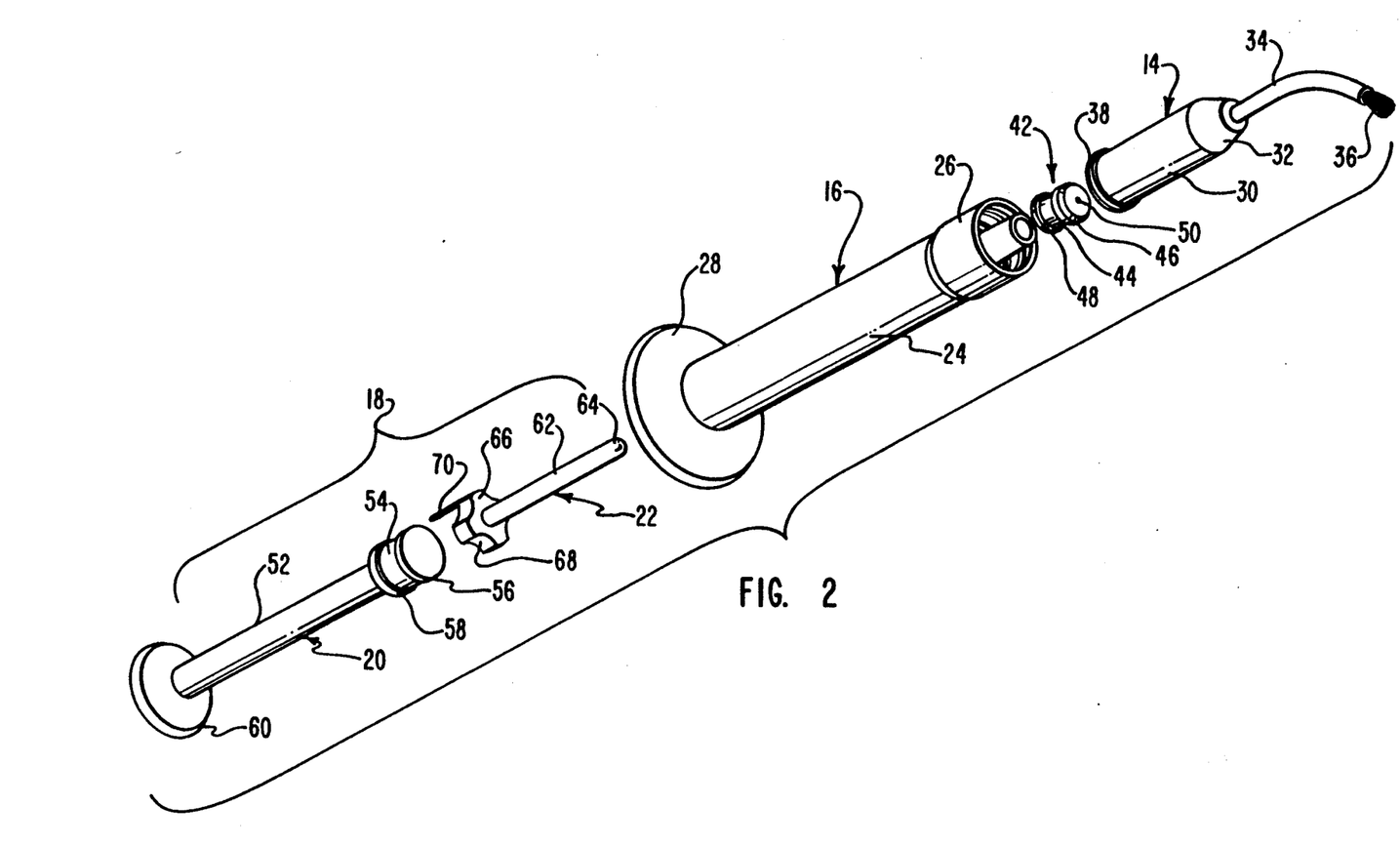
FIG. 2 is an exploded perspective view of the syringe apparatus of the present invention illustrating the separate components and the assembly of the preferred embodiment.

With reference first to FIGS. 1 and 2 taken together, the overall syringe apparatus is generally designated at 10. In one aspect of the invention, the syringe apparatus 25 is comprised of a barrel means that forms first and second chambers and wherein the second chamber is adapted for receiving first and second substances that are to be mixed therein and then subsequently delivered to a desired surface. In the illustrated embodiment, the barrel means is shown by way of example at the bracket indicated at reference numeral 12 in FIG. 1, and is further comprised of a standard syringe barrel which is generally designated at 16 and a mixing and delivery tip which is generally designated at 14.

In another aspect of the invention, the syringe apparatus is also comprised of a plunger means, which is illustrated by way of example at the bracket 18 in FIG. 2. The plunger means in turn is comprised of a primary plunger member which is generally designated at 20 and a secondary plunger member which is generally designated at 22.

Figure 4:
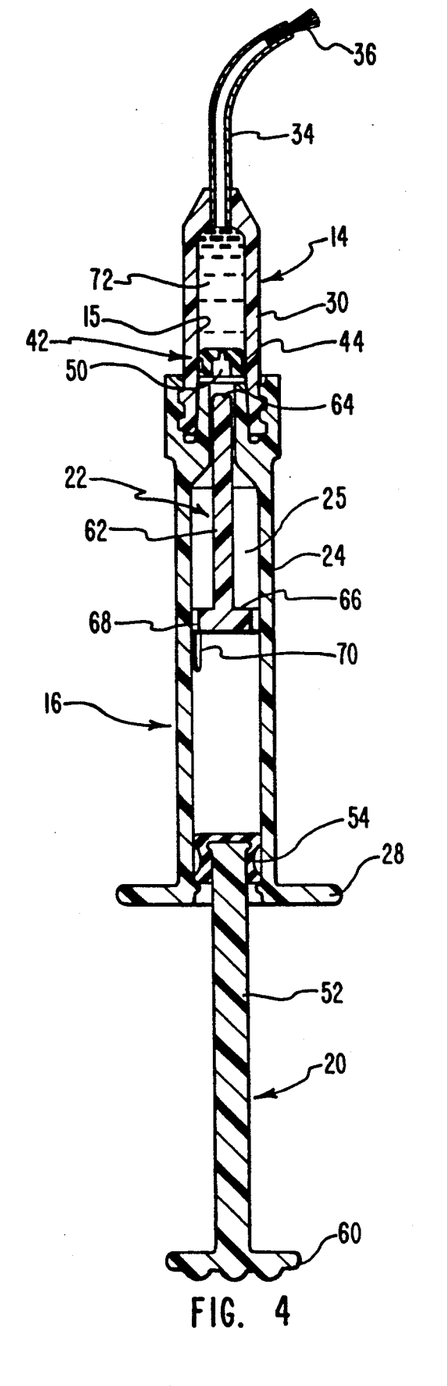
FIG. 4 is a cross-sectional view of the syringe apparatus taken along line 4—4 of FIG. 1, and wherein the primary plunger is fully retracted and the secondary plunger is in a forward position such that the aeration of the substances contained within the mixing tip chamber can occur by the single downward stroke of the primary plunger into the syringe barrel through a first distance.

With continued reference principally to FIG. 2, the syringe barrel generally designated at 16 has an elongated syringe body 24 which, as shown best in FIGS. 1 and 4, forms an enclosure for a first chamber 25. At the distal end of the syringe body 24 there is a threaded luer coupling member 26. At the proximal end of the syringe body 24, there is a generally circular, flat disc 28 formed around the inlet opening to the syringe body 24 and which is used for purposes of applying finger pressure when pushing the primary syringe plunger 20 through the syringe barrel 16.

Still referring principally to FIG. 2, a separately couplable mixing and delivery tip 14 is comprised of an elongated body 30 which is conically tapered at its distal end as shown at 32 and which terminates in a slender, curved delivery tip 34 which has applicator bristles 36 extending out of the end thereof. The proximal end of the elongated body 30 has a threaded luer coupler 38 which is adapted to be coupled to the threaded luer coupling 26 on the syringe barrel 16 so that the mixing and delivery tip 14 can be joined at the distal end of the syringe barrel 16. Thus, coupling members 38 and 26 together serve as a coupling means. Delivery tip 34 could, of course, be any type of tip, with or without bristles, or with a needle, as required for a particular application.

As shown best in FIGS. 1 and 4, the interior of the elongated body 30 forms a second chamber 15 which is adapted for receiving first and second substances to be mixed therein. As hereinafter more fully described, the substances which are to be mixed could be any type of fluids, such as a liquid which is to be mixed with air, two different liquids which are to be mixed together, or a liquid and a solid or powdered substance which are to be mixed together.

Disposed between the first chamber 25 of the syringe barrel 16 and the second chamber 15 of the mixing and delivery tip 14 is a slidable valve or secondary piston which is generally indicated at reference numeral 42. The valve or secondary piston 42 is preferably constructed of a soft, elastomeric material and is dimensionally sized so that the rings 46 and 48 which are disposed at opposite ends of the valve body 44 will form a fluid-tight fit when placed within the second chamber 15 of the mixing and delivery tip 14. The valve or secondary piston 42 also has an aperture 50 formed through the center of it, which is shown best in FIGS. 2, 4, and 8 taken together.

Figure 8:
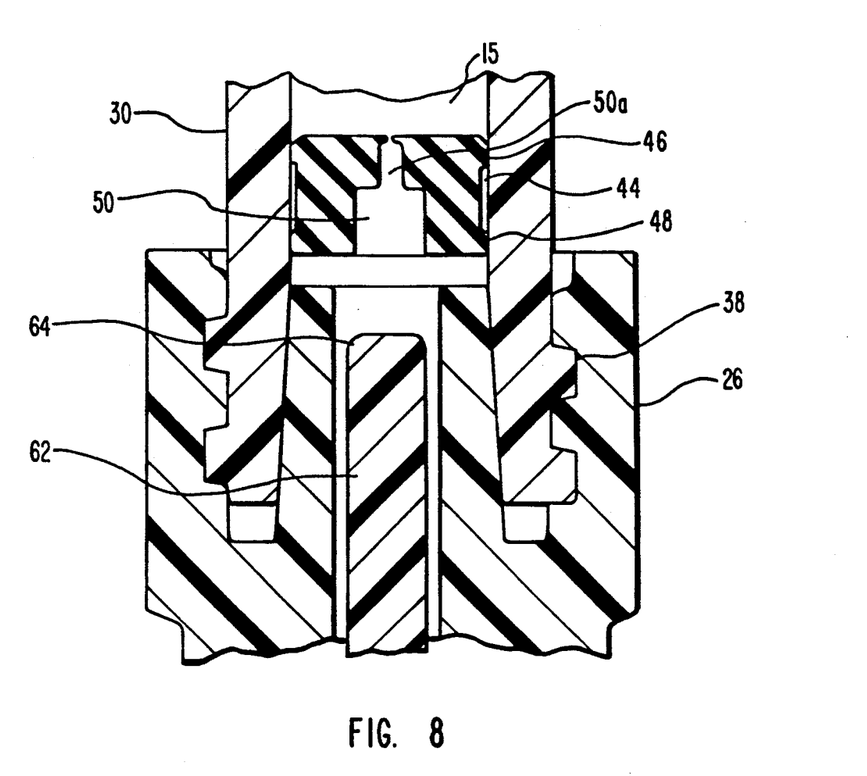
FIG. 8 is an enlarged cross-sectional view of a portion of FIG. 4 more particularly illustrating the slidable valve or secondary piston.

With particular reference to FIG. 8, the aperture 50 is diameterally enlarged through a portion of the valve or secondary piston 42 so as to receive the distal end 64 of piston rod 62 of the secondary plunger member 22. A second portion of the aperture 50 which is illustrated at 50 in FIG. 8 is smaller in diameter and extends through the upper portion of the valve or secondary piston 42. The aperture 50, as more particularly described hereinafter, provides for passage of air to and from the second chamber 15.

With reference again to FIG. 2, the primary plunger member generally designated at 20 is comprised of an elongated piston rod 52 which has an elastomeric piston 54 at the distal end thereof. The piston 54 has enlarged rings 56 and 58 which form a fluid-tight fit when inserted into the first chamber 25 of the syringe barrel 16. The proximal end of the piston rod 52 has an enlarged circular disc 60 attached to it to which force is applied for purposes of pushing the plunger 20 into the syringe barrel 16.

The secondary plunger member generally designated at 22 also has an elongated piston rod 62 which has a rounded distal end at 64. As shown best in FIG. 8, the diameter of the piston rod 62 is slightly larger than the aperture 50 so that as the distal end 64 of the piston rod 62 is pushed into the aperture 50 the body 44 and enlarged rings 46 and 48 of the valve or secondary piston 42 will be urged more tightly against the walls of the second chamber 15 to thereby form a fluid-tight fit such that the contents of the second chamber 15 can thereafter be expelled as the valve or secondary piston 42 is pushed through the second chamber 15.

The proximal end of the piston rod 62 on secondary plunger member 22 has a disc 66 attached to it. As shown best in FIGS. 2 and 9 taken together, the disc 66 is generally circular in configuration, but has four arcuate portions as shown at 68 removed so that the disc 66 does not form a fluidtight fit within the first chamber 25. Thus, as will be hereinafter more fully described, as the first plunger member 20 begins to slide through the first chamber 25 in the syringe barrel 16, air is pressurized and is permitted to flow around the secondary plunger member 22 by means of the arcuate openings 68 formed around the periphery of disc 66 (see FIG. 9).

Figure 9:
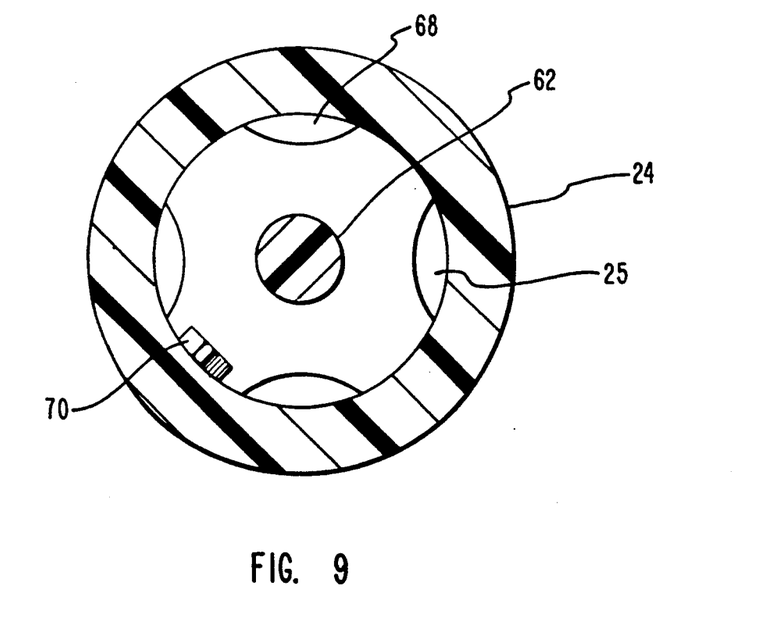
FIG. 9 is an enlarged cross-sectional view of a portion of FIG. 1 taken along line 9—9 illustrating the air flow passageways around the buttress end of the secondary plunger.

Also attached at an edge of disc 66 is a spike 70 which, as hereinafter more fully described, may be used to release the fluid-tight seal otherwise formed by the piston 54 of the primary plunger member 20.

Figure 3:
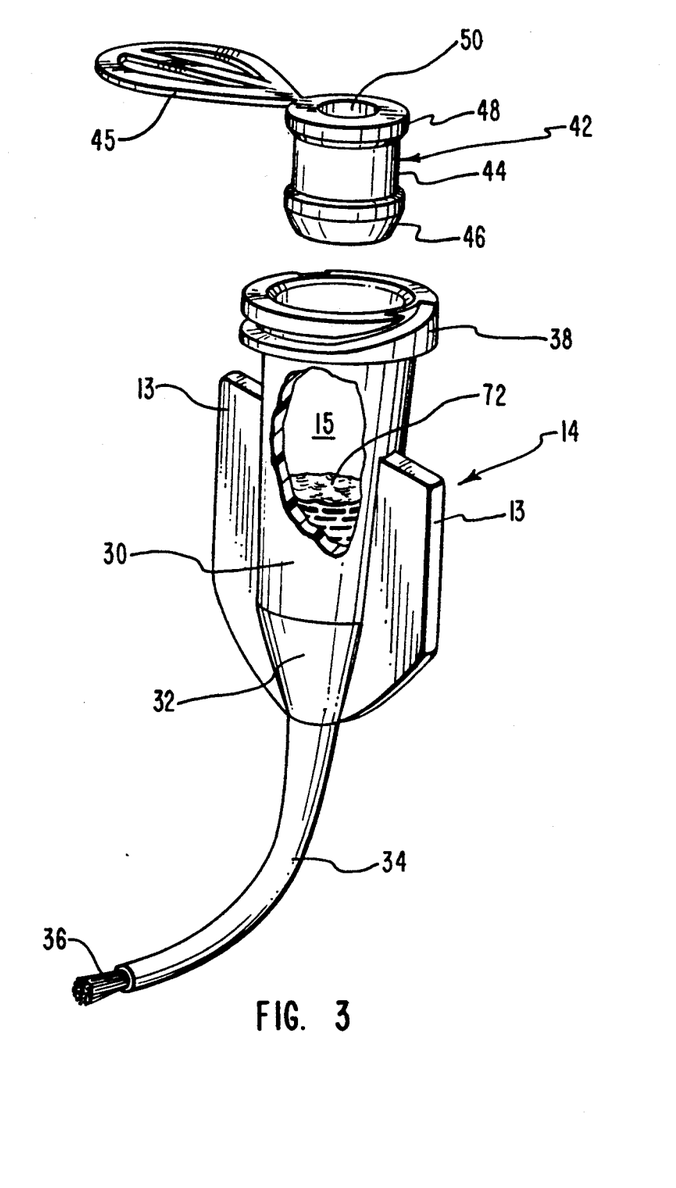
FIG. 3 is an enlarged perspective view with portions broken away to more particularly illustrate placement of two or more substances into the delivery and mixing tip followed by closure of the proximal end of the delivery and mixing tip by the slidable valve or secondary piston.

Reference is next made to FIGS. 3–6 taken together, which collectively illustrate several methods for using the syringe apparatus of the present invention. As shown first in FIG. 3, a mixing and delivery tip generally designated at 14 such as that described above is placed so that two different substances can be loaded into the second chamber 15. The mixing and delivery tip 14 of FIG. 3 is essentially identical to that described above except for the addition of the wings 13 which facilitate attachment of the luer couplings 38 and 26. The two substances which are loaded into the second chamber 15 are illustrated in FIG. 3 as constituting two liquids which are shown at reference numeral 72. However, as noted above, the substances which are to be mixed can be comprised of two liquids, a single liquid which is to be mixed with air or a liquid and a solid or powdered medicament which are to be mixed.

In one preferred method for using the apparatus, after the two substances are loaded into the second chamber 15 of the mixing and delivery tip 14, the valve or secondary piston 42 is then pushed into the end of the second chamber 15 to enclose it. In the embodiment illustrated in FIG. 3, the valve or secondary piston 42 has a temporary finger tab 45 attached to the side of it to facilitate placement into the second chamber 15, the finger tab 45 thereafter being easily detachable and removable. As the valve or secondary piston 42 is inserted into the opening at the proximal end of the second chamber 15, air is permitted to escape through the aperture 50 so that the contents of the second chamber 15 are not forced out of the delivery tip 34 and applicator brush 36. Once the valve or secondary piston 42 has been seated in the proximal end of the second chamber 15, the entire assembly is then coupled by means of the threaded luer couplings 38 and 26 so as to join the mixing and delivery tip 14 to the syringe barrel 16.

With reference next to FIG. 4, the primary plunger member 20 is shown fully retracted so that the piston 54 is situated at the inlet opening or proximal end of the syringe barrel 16. In this position, the primary plunger member 20 can then be actuated so as to move the piston 54 at the end of plunger rod 52 through the first chamber 25 of syringe barrel 16 for a first distance. Because of the fluid-tight fit created between the elastomeric piston 54 and the interior sidewalls of the syringe barrel 16, as the piston rod 52 is moved through the first distance, air is pressurized in the first chamber 25. As will be further seen from FIG. 4, the piston rod 62 of the secondary plunger member 22 is smaller in diameter throughout its length than the smallest diameter of the first chamber 25 so that the pressurized air flows around the secondary plunger member 22 by virtue of the arcuate openings 68 and small diameter or rod 62, and then through the remaining space of the second chamber 25 up through the aperture 50 in the valve or secondary piston 42. In this manner, the pressurized air is injected into the fluids contained in the second chamber 15. The injection of the air is shown at 74 in FIG. 5. The injected air 74 in turn will cause a turbulent aeration and mixing of the fluids contained in the second chamber 15.

Figure 5:
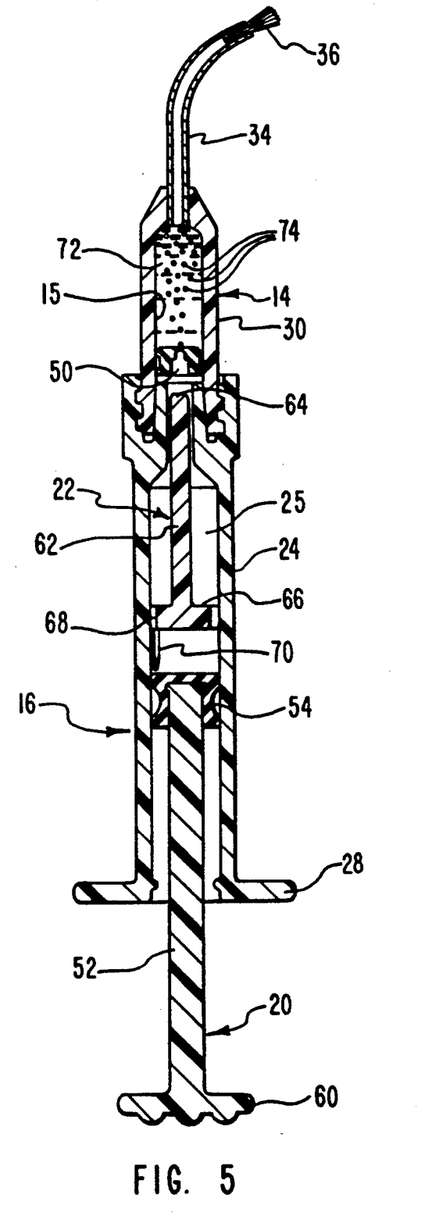
FIG. 5 is a cross-sectional view of the syringe apparatus of the present invention illustrating the primary plunger at the end of the first distance and the aeration caused in the mixing chamber.
Figure 6:
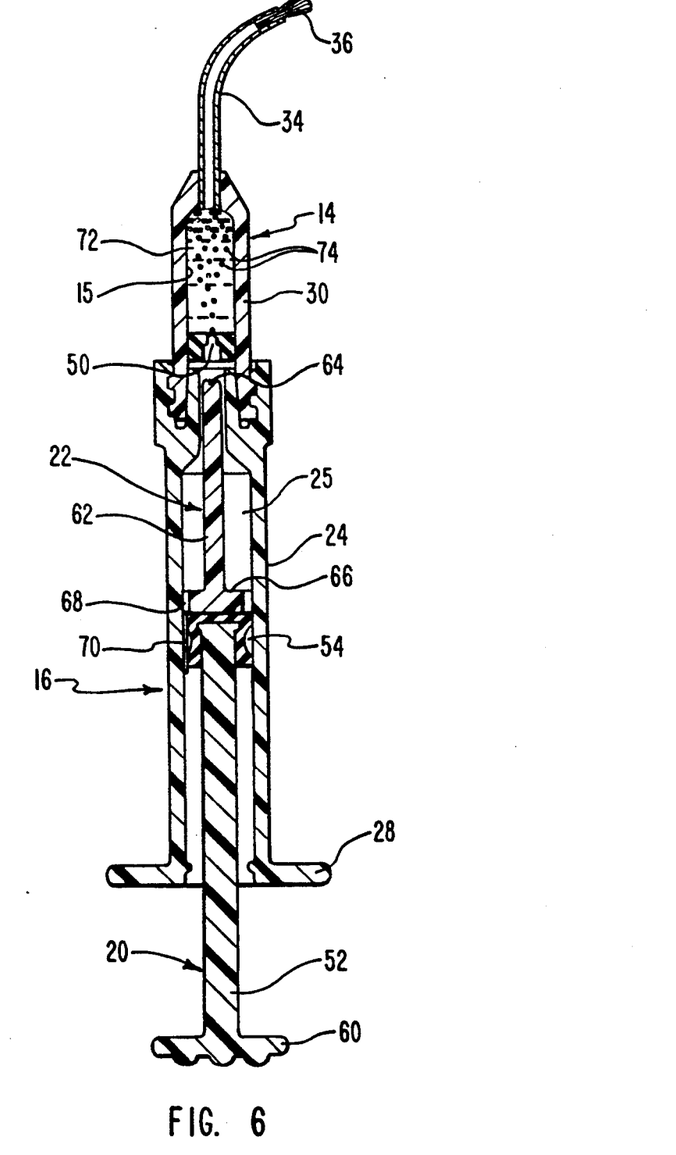
FIG. 6 is a cross-sectional view of the syringe apparatus wherein the primary and secondary plungers are fully engaged so that continued movement of the primary plunger causes tandem movement of the secondary plunger, and wherein the fluid-tight seal of the primary plunger is released to prevent continued pressurization of air.
Figure 7:
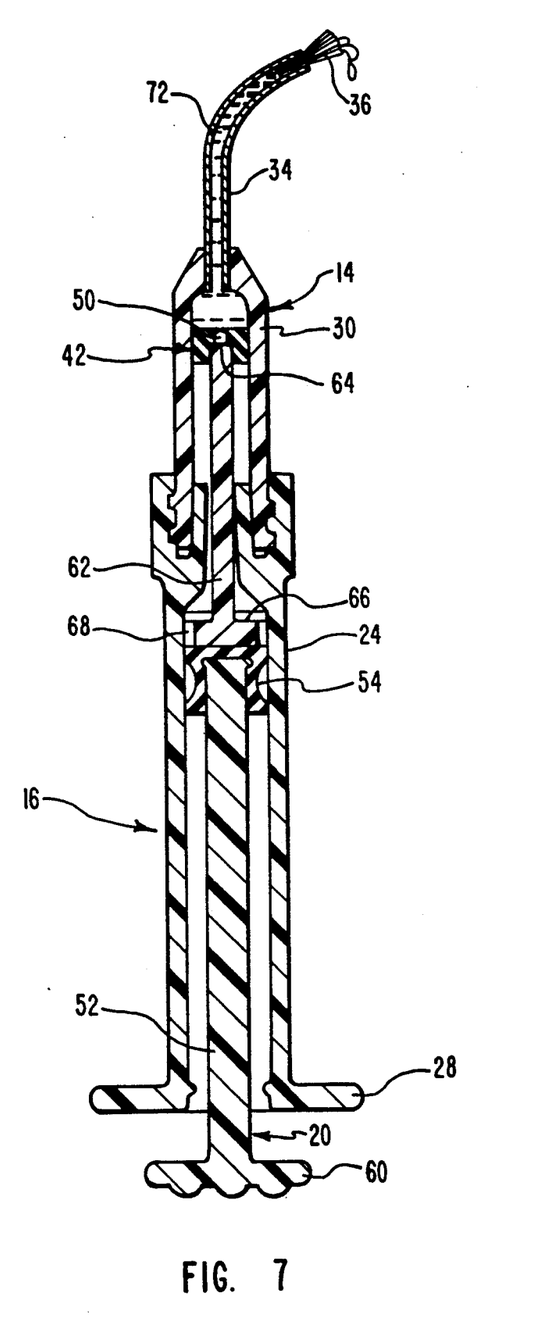
FIG. 7 is a cross-sectional view of the syringe apparatus illustrating tandem movement of the primary and secondary syringe plungers together so as to cause the secondary syringe plunger to first seal the slidable valve positioned in the delivery and mixing tip and so as to thereafter effect delivery of the mixed substances by continued tandem movement of the primary and secondary syringe plungers.

As the primary plunger member 20 reaches the end of the first distance, which is shown in FIG. 5, the turbulent aeration is terminated because thereafter further movement of the primary plunger member 20 as shown in FIG. 6 causes the elastomeric piston 54 to ride up and over the spike 70. This releases any pressurized air so that continued pressurization of air no longer occurs. Thereafter, continued movement of the primary plunger member 20 through a second distance through the length of the syringe barrel 16 causes the secondary plunger member 22 to thereafter move in tandem with the first plunger member 20. Continued movement of the primary plunger member 20 and corresponding movement of the secondary plunger member 22 then causes the distal end 64 of the piston rod 62 to become seated within the valve or secondary piston 42 as previously described, closing off the aperture 50 and more tightly sealing the valve or secondary piston 42 within the second chamber 15. Continued application of force on the primary plunger member 20 then causes the contents of the second chamber 15 to be expelled through the delivery tip 34 and applicator brush 36 as illustrated in FIG. 7.

In a second preferred method of using the apparatus of the present invention, in the case where highly viscous substances or where a liquid and a solid substance are loaded into the mixing and delivery tip 14 such that mixing by means of turbulent aeration is not possible, the contents of the mixing and delivery tip 14 can be mechanically mixed prior to placing the valve or secondary piston 42 into the proximal end of the second chamber 15 (See FIG. 3). This mechanical mixing may be done, for example, by using a small stir rod (not shown). Thereafter, the valve or secondary piston 42 is placed into the proximal end of the second chamber 15 and the mixing and delivery tip 14 is then connected to the syringe barrel 16 as before. However, when using the syringe apparatus in this fashion, before the mixing and delivery tip 14 is connected to the syringe barrel 16, primary plunger member 20 and secondary plunger member 22 are first placed into direct contact with each other such as shown by the position in FIG. 6 so that application of force on the primary plunger member 20 will cause the secondary plunger member 22 to move in tandem, first sealing the aperture 15 and then moving the valve or secondary piston 42 through the second chamber 15 to effect delivery of the contents thereof.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters patent is:

1. A syringe apparatus comprising:
    barrel means forming first and second chambers, said second chambers adapted for receiving first and second substances to be mixed therein;
    valve means situated in the barrel means between the first and second chambers for providing passage of air into and out of the second chamber; and
    plunger means, slidably disposed in said barrel means, for sealing the valve means to prevent passage of air therethrough and for expelling the mixed substances from said second chamber as said plunger means is pushed into said barrel means, and wherein said plunger means comprises:
        a first plunger member comprising a distal end with a piston mounted thereon, the distal end and piston being slidably disposed within said first chamber; and a second plunger means separate and unattached from the first plunger member so as to be moveable only in tandem with the first plunger member once contacted by the first plunger member, and comprising a distal end for contacting the valve means and for sealing the valve means as said contact is made, and further comprising a proximal end slidably situated in said first chamber so as to be contacted by said piston at the distal end of the first plunger member, the distal end of said second plunger member thereafter being moveable through said second chamber by continued movement of the first plunger member.

2. A syringe apparatus as defined in claim 1 wherein said barrel means comprises:

a syringe barrel which is hollow so as to form said first chamber within the syringe barrel, said syringe barrel comprising a distal end having an outlet opening and a first coupling member, and further comprising a proximal end with an inlet opening for slidably receiving said piston; and a mixing and delivery tip which is hollow so as to form said second chamber, said mixing and delivery tip comprising a distal end having a delivery means through which the mixed substances are delivered to a desired surface, and further comprising a proximal end with an inlet opening slidably sealed by said valve means and a second coupling member securable to the first coupling member so as to join the mixing and delivery tip to the distal end of the syringe body.

3. A syringe apparatus as defined in claim 2 wherein the syringe barrel and mixing and delivery tip are formed of transparent material.

4. A syringe apparatus as defined in claim 1 wherein said valve means comprises a piston having an aperture for passage of air into and out of the second chamber, and which is adapted to be sealed when contacted by the distal end of said second plunger member.

5. A syringe apparatus as defined in claim 4 wherein each said piston is formed of an elastomeric material.

6. A syringe apparatus comprising:

a barrel enclosing a first chamber therein;

a mixing and delivery tip enclosing a second chamber containing fluids to be mixed therein and then delivered to a desired surface;

coupling means for securing said mixing and delivery tip to said barrel;

valve means situated between said first and second chambers for providing passage of air to and from said second chamber;

primary plunger means extending partially into said first chamber for selective application of pressure so that as the primary plunger means is pushed into the first chamber through a first distance, pressurized air is injected from the first chamber through the one-way valve means into the second chamber so as to create mixing turbulence within the fluids contained in the second chamber; and secondary plunger means separate and unattached from the first plunger member so as to be slidable within the second chamber to engage and seal said valve means only once the primary plunger means contacts the secondary plunger means, with continued movement of the primary plunger means through the first chamber for a second distance also causing movement of the secondary plunger means and movement of the sealed valve means through the secondary chamber so as to terminate the turbulence and expel the contents of the second chamber.

7. A syringe apparatus as defined in claim 6 wherein said barrel is constructed of transparent material and comprises an inlet opening at a proximal end thereof, and wherein said coupling means comprises a first threaded luer coupling at a distal end of said barrel.

8. A syringe apparatus as defined in claim 7 wherein said mixing and delivery tip is constructed of transparent material and comprises an applicator means at a distal end thereof through which mixed fluids are delivered to a desired surface, and wherein said coupling means further comprises a second threaded luer coupling at a proximal end of said mixing tip for connection to said first luer coupling.

9. A syringe apparatus as defined in claim 6 wherein said valve means comprises a piston having an aperture through which said pressurized air is injected, and which is adapted to be sealed when contacted by said secondary plunger means.

10. A syringe apparatus as defined in claim 9 wherein said piston is formed of an elastomeric material.

11. A syringe apparatus as defined in claim 6 wherein said primary plunger means comprises a first plunger rod having an elastomeric piston at a distal end thereof, said piston slidably disposed in said first chamber in a fluid-tight manner, and a proximal end with a generally flat member to which force is applied to move the piston through the first chamber.

12. A syringe apparatus as defined in claim 11 wherein said secondary plunger means comprises a second plunger rod having a distal end adapted for contact and sealing of said valve means, and further comprises a proximal end with a disc thereon slidably disposed in said first chamber in a non-fluid-tight manner, and to which force is applied by the piston of said first rod to slidably move the second rod.

13. A syringe apparatus as defined in claim 12 further comprising means for breaking the fluid-tight seal of said piston in the first chamber as the piston contacts the disc at the proximal end of the second plunger rod.

14. A syringe apparatus as defined in claim 13 wherein the means for breaking the fluid-tight seal comprises a spike attached to an edge of the disc at the proximal end of the second plunger rod.

15. A syringe apparatus comprising:

a transparent barrel which forms a first chamber therein, the barrel having a first coupling member at a distal end thereof and having an inlet opening at a proximal end thereof;

a transparent mixing tip which forms a second chamber for holding fluids to be mixed therein, and having a delivery tip at a distal end thereof for delivery of the mixed fluids to a desired surface, and having a second coupling member at a proximal end thereof which is couplable to the first coupling member so as to join the mixing tip to the barrel;

an elastomeric piston disposed in the second chamber, said piston having an aperture formed therethrough for providing passage of air into and out of the second chamber so as to create turbulence and mixing of the fluids in the second chamber as air enters the second chamber;

a first plunger member inserted through the inlet opening of the barrel and separately moveable through the first chamber for a first distance, said first plunger member comprising a first piston rod with an elastomeric piston disposed at a distal end thereof in fluid-tight engagement with said first chamber, and further comprising a generally flat member at a proximal end thereof situated outside of the first chamber and to which force is applied to move the piston through the first chamber;

a second plunger member moveable only in tandem with the first plunger member through a second distance, said second plunger member comprising a second piston rod with a distal end adapted to contact and seal the aperture in the elastomeric piston disposed in the second chamber, and further comprising a disc at a proximal end of the second piston rod to which force is applied by the piston at the distal end of the first piston rod when moving the second plunger member in tandem with the first plunger member through the second distance, and further comprising a spike attached at an edge of the disc; and whereby as the first plunger member is moved through the first distance air is pressurized and forced through the aperture in the elastomeric piston disposed in the second chamber to create a mixing turbulence in the fluids therein, and as the first plunger member is moved through the second distance, the spike breaks the fluid-tight seal of the piston at the distal end of the first plunger rod, and the piston at the distal end of the first plunger rod contacts the disc so as to move the second plunger member in tandem with the first plunger member, causing the distal end of the second plunger rod to seal the aperture and push the piston in the second chamber through the second chamber to expel the mixed fluids.

16. A syringe apparatus comprising:
a barrel enclosing a first chamber therein;
a mixing and delivery tip enclosing a second chamber containing fluids to be mixed therein and then delivered to a desired surface;
coupling means for securing said mixing and delivery tip to said barrel;
valve means situated between said first and second chambers for providing passage of air to and from said second chamber;
primary plunger means extending partially into said first chamber for selective application of pressure so that as the primary plunger means is pushed into the first chamber through a first distance, pressurized air is injected from the first chamber through the one-way valve means into the second chamber so as to create mixing turbulence within the fluids contained in the second chamber said primary plunger means comprising a first plunger rod having an elastomeric piston at a distal end thereof, said piston slidably disposed in said first chamber in a fluid-tight manner, and a proximal end with a generally flat member to which force is applied to move the piston through the first chamber; and
secondary plunger means slidable within the second chamber for engaging and sealing said valve means such that as the primary plunger means contacts the secondary plunger means, continued movement of the primary plunger means through the first chamber for a second distance will also cause movement of the secondary plunger means and movement of the sealed valve means through the secondary chamber so as to terminate the turbulence and expel the contents of the second chamber, said secondary plunger means comprising a second plunger rod having a distal end adapted for contact and sealing of said valve means, and further comprising a proximal end with a disc thereon slidably disposed in said first chamber in a non-fluidtight manner, and to which force is applied by the piston of said first rod to slidably move the second rod.

* * * * *

UNITED STATES PATENT AND TRADEMARK OFFICE
CERTIFICATE OF CORRECTION

PATENT NO. : 5,286,257
DATED : February 15, 1994
INVENTOR(S) : DAN E. FISCHER

It is certified that error appears in the above-indentified patent and that said Letters Patent is hereby corrected as shown below:

Title page, Abstract, line 8, "secondchamber" should be --second chamber--
Column 6, line 60, "fluidtight" should be --fluid-tight--
Column 9, line 3, "means" should be --member--

Signed and Sealed this

Fifteenth Day of November, 1994

Attest:

BRUCE LEHMAN

*Attesting Officer*   *Commissioner of Patents and Trademarks*